United States Patent [19]

Ladin

[11] Patent Number: 5,792,090
[45] Date of Patent: Aug. 11, 1998

[54] OXYGEN GENERATING WOUND DRESSING

[76] Inventor: Daniel Ladin, 1411 Ferdon Rd., Ann Arbor, Mich. 48104

[21] Appl. No.: 490,749

[22] Filed: Jun. 15, 1995

[51] Int. Cl.$^6$ .................................................. A61F 5/00
[52] U.S. Cl. .......................... 602/48; 604/304; 424/449
[58] Field of Search ............................ 424/443, 445, 424/447, 449, 639; 602/41–58; 604/304

[56]            References Cited

U.S. PATENT DOCUMENTS

| 4,507,285 | 3/1985  | Kühne          | 424/130    |
|-----------|---------|----------------|------------|
| 4,549,969 | 10/1985 | Gerlach et al. | 210/79     |
| 4,703,108 | 10/1987 | Silver et al.  | 530/356    |
| 4,837,285 | 6/1989  | Berg et al.    | 530/356    |
| 4,875,473 | 10/1989 | Alvarez        | 128/155    |
| 4,965,989 | 10/1990 | Ellis          | 55/162     |
| 4,994,049 | 2/1991  | Latzke et al.  | 604/307    |
| 5,029,579 | 7/1991  | Trammell       | 128/205.26 |
| 5,064,422 | 11/1991 | Wick           | 604/307    |
| 5,147,339 | 9/1992  | Sundström      | 604/307    |
| 5,227,168 | 7/1993  | Chvapil et al. | 421/445    |
| 5,336,209 | 8/1994  | Porzilli       | 604/307    |
| 5,407,685 | 4/1995  | Malchesky et al. | 424/449  |
| 5,578,022 | 11/1996 | Scherson et al. | 604/304   |

OTHER PUBLICATIONS

"Skin Permeability to Oxygen and Hyperbaric Oxygen", Ronald P. Gruber, et al. *Arch. Dermatol.*, vol. 101, Jul., 1970, pp. 69–70.

"Combination of Hyperbaric Oxygen, Surgery, and Antibiotics in the Treatment of Clostridial Gas Gangrene", Juha Niinikoski, M.D., and Allan J. Aho, M.D. *Infections in Surgery*, Jan., 1983, pp. 23–37.

"Physiological Effects of Tissue Oxygenation on Wound", JoAnne D. Whitney, R.N., M.S., *Heart & Lung*, vol. 18., No. 5, Sep., 1989, pp. 466–474.

"A Simplified Hyperbaric Oxygen Technique for Leg Ulcers", Madalene C. Y. Heng, et al, *Arch. Dermatol.*, vol. 120, May, 1984, pp. 640–645.

"The Microlcimate Chamber: Morphological Aspects of Experimental Deep Burns Treated Topically with Continuous Humidified Oxygen", Theodor Kaufman, M.D., et al, *Annals of Plastic Surgery*, vol. 10, No. 3, Mar. 1983.

"Clinical Case Studies of the Topox Chamber 'Portables'" of The Topox Corporation, Jersey City, NJ.

"Hyperbaric Oxygen Therapy for Pyoderma Gangrenosum", M.C.Y. Heng, *Aust. NZ J. Med.*, vol. 14, 1984, pp. 618–621.

"Topical Hyperbaric Oxygenation in the Treatment of Recalcitrant Open Wounds—A Clinical Report", A. Valentino Upson, *Physical Therapy*, vol. 66, No. 9, Sep., 1986, pp. 1408–1411.

"Hyperbaric Oxygen Application Can Heal Wounds Faster", Frederic J. Vagnini, M.D., F.A.C.S., *N.Y. Hospital & Health News*, Dec., 1990.

"Topical Hyperbaric Therapy for Problem Skin Wounds", Madalene C.Y. Heng, *J. Dermatol. Surg. Oncol.*, 1993, pp. 784–793.

(List continued on next page.)

*Primary Examiner*—Richard J. Apley
*Assistant Examiner*—Kim M. Lee
*Attorney, Agent, or Firm*—Brooks & Kushman

[57]            ABSTRACT

The healing of surface wounds, including burns, is facilitated by increasing the wound oxygen tension through the application of an oxygen-generating wound dressing which renewably and non-sustainingly chemically generates oxygen. The wound dressing contains an oxygen permeable membrane and an oxygen supply solution reservoir adapted to receive an aqueous liquid capable of supplying oxygen through chemical reaction. Preferably, the aqueous liquid contains hydrogen peroxide and the reservoir contains an immobilized solid hydrogen peroxide decomposition catalyst such as manganese dioxide. The solid catalyst may be contained within a hydrogel, an open-celled polymeric foam, or a biosynthetic foam such as a collagen foam. The oxygen-generating wound dressing may be applied over an intermediate hydrogel occlusive wound covering such as an alginate.

20 Claims, 8 Drawing Sheets

OTHER PUBLICATIONS

"Hyperbaric Oxygen Therapy for a Foot Ulcer in a Patient with Polyarteritis Nodosa", Madalene C.Y. Heng, *Aust. J. Derm.*, (1983) vol. 24, No. 105, pp. 105–108.

"Treatment of Ulcers on the Legs with Hyperbaric Oxygen", Boguslav H. Fischer, M.D., *J. of Derm. Surg.*, vol. 1, No. 3, Oct., 1975, pp. 55–58.

"Topical Oxygen Promotes Healing of Leg Ulcers", Stanley Olejniczak, M.D., and Andrew Zelinski, M.D., Ph.D., *Medical Times*, vol. 104, No. 12, Dec., 1976, pp. 114–120.

"Topical Oxygen and Burn Wound Healing: A Review", Theodor Kaufman, et al.

"Topical Hyperbaric Oxygen Therapy", Billie Jackson, et al. Presented at the Scientific Study Area at: 1987 A.A.D. Meeting, Veterans Hospital Hospital, Memphis, TN and University of Tennessee.

"Oxygen and Tissue Repair", I. A. Silver, Dept. of Pathology, Medical School, University of Bristol, Bristol, UK, *An Environment for Healing: The Role of Occlusion* ed. T. J. Ryan: Royal Society of Medicine International Congress and Symposium Series No. 88, Published by the Royal Society of Medicine.

OXYGEN GENERATING WOUND DRESSING

TECHNICAL FIELD

The present invention pertains to wound dressings. More particularly, the subject invention pertains to wound dressings which chemically generate oxygen in situ, and thus are capable of producing periodic oxygen tensions similar to those obtained in topical hyperbaric oxygen treatment followed by quiescent periods.

BACKGROUND ART

The healing of wounds and the effect of oxygen tension has been intensively studied. A useful summary is presented in J. D. Whitney, "Physiologic Effects of Tissue Oxygenation on Wound Healing", HEART & LUNG, September 1989, Vol. 18, No. 5, pp. 466–474. Among the components important in the healing process are fibroblast proliferation, angiogenesis, collagen synthesis, and reepithelialization.

Soon after injury, whether accidental or surgically induced, undifferentiated mesenchymal cells transform to migratory fibroblasts which migrate into and across the injured wound. It is known that fibroblasts are aerobic in nature. Fibroblasts are stimulated to produce collagen. While experiments from cultured fibroblasts suggest that high lactate and ascorbic acid concentration typical of hypoxic conditions may activate some of the fibroblast collagen-synthesizing enzymes, animal studies involving low, normal, and high oxygen tensions nevertheless demonstrate increased rates of collagen synthesis under hyperoxic rather than hypoxic conditions.

Angiogenesis, on the other hand, appears to be stimulated by a hypoxic tissue gradient, with new capillaries extending in the direction of lower oxygen concentration. When a hypoxic gradient no longer exists, angiogenesis is minimized or static. Epithelialization is also known to be related to oxygen tension, with higher rates of epithelial proliferation observed under hyperoxic as opposed to hypoxic conditions.

The supply of oxygen to healing wound tissue may be derived from three sources: oxygen chemically bound to hemoglobin in whole blood; oxygen dissolved in plasma; and oxygen which diffuses into plasma or tissue from the exterior. In deep wounds, the latter is of little importance. The studies of R. P. Gruber et al., "Skin Permeability to Oxygen and Hyperbaric Oxygen", ARCH. SURG., Vol. 101, July 1970, pp. 69–70, for example, indicate that oxygen tension, measured polarographically, increases markedly at 3 bar of 100% $O_2$ in the superficial dermis (0.30–0.34 mm), while the relative oxygen concentration of the deep dermis (1.8–2.2 mm) is unchanged under the same conditions.

In surface wounds, all sources of oxygen are important. In wounds of large surface area, however, for example ulcers, only the tissue at the edges of the ulcer or at its base are well supplied with blood, and the growing granulation tissue, in the absence of oxygen diffusing from the exterior, must be supplied by diffusion from blood vessels and plasma, a relatively inefficient process.

It is well established, also, that occlusive coverings promote wound healing. W. H. Eaglstein, "Experiences with Biosynthetic Dressings", J. AM. ACAD. DERMATOL., February 1985, 12 pp. 434–40. Furthermore, it is well known that the changing of wound dressings may interfere with the healing process by disrupting the healing tissue where granulation and collagen synthesis has not imparted sufficient tensile strength to avoid rupture upon dressing removal. However, due to the inability of the blood and plasma to supply optimal oxygen concentration, and due to the further reduction in oxygen from the exterior brought about by the presence of the occluding dressing, a hypoxic condition may rapidly be reached. Although this condition may encourage angiogenesis, it negatively affects collagen synthesis and epithelialization. Moreover, various clostridium species, e.g. $C.\ perfringens$, and $C.\ septicum$ are induced to germinate under hypoxic conditions, which can also support other anaerobic flora. J. Niinikoski et al., "Combination of Hyperbaric Oxygen, Surgery, and Antibiotics in the Treatment of Clostridial Gas Gangrene", INFECTIONS IN SURGERY, January 1983, pp. 23–37. In addition to minimizing anaerobic flora by discouraging germination, hyperoxic conditions are known to reduce the concentration of other pathogens as well.

Past treatment of chronic ulcers and gangrenous tissue has, in many cases, involved extensive debridement in combination with antibiotics and systemic hyperbaric oxygen. Room size hyperbaric oxygen chambers or chambers sized for the individual patient have employed pure oxygen at pressures of 2 to 3 bar. Treatment time is limited, as oxygen toxicity and CNS disorders may result from the increased oxygen content of the blood. Such treatments have met with a great deal of success, but the success may not be due to the increased systemic blood and plasma-derived oxygen supply. The blood and plasma already contain sufficient oxygen for the healing process. Rather, it is the diffusion-limited access of oxygen to the wound which limits the oxygen supply required for optimal healing and minimization of infection. The increased oxygen tension in the wound most likely results directly from increased diffusion into the wound surface from the oxygen in the chamber. Gruber, for example, indicates that rate of oxygen absorption from the skin is roughly proportional to oxygen concentration from nearly 0% to 30%. Gruber further indicates, however, that oxygen absorption tends to level off at higher oxygen concentrations.

Due to the expense of large hyperbaric chambers and the systemic effects of oxygen toxicity which they may engender, topical hyperbaric chambers have been proposed. Topical chambers operating at "normal" hyperbaric pressures of 2–3 bar are difficult to seal to the body or extremity being treated, however, without interfering with blood supply to the wound locus. Thus, hyperbaric chambers operating at only modestly elevated pressure have been manufactured. One such device, operating at 22 mm Hg pure oxygen (1.03 bar) is shown in B. H. Fischer, "Treatment of Ulcers on the Legs with Hyperbaric Oxygen", J. OF DERM. SURG., 1:3, October 1975, pp. 55–58, on page 56. However, as indicated in M. C. Y. Heng et al., "A Simplified Hyperbaric Oxygen Technique for Leg Ulcers", ARCH. DERMATOL., Vol 120, May 1984, pp. 640–645, such chambers are expensive and difficult to sterilize. Cross-infection is stated to be common.

Heng and others have proposed a simple hyperbaric oxygen treatment chamber consisting of a polyethylene bag which may be secured to the body or extremity with adhesive tape (Heng, op. cit.), or a transparent nylon bag with straps and VELCRO™ closure. S. Olejniczak et al., "Topical Oxygen Promotes Healing of Leg Ulcers", MEDICAL TIMES, Vol. 104, No. 12, pp. 114–121. Pressure is maintained at between 20 mm Hg and 30 mm Hg. However, the leakage associated with the sealing of such bags requires a relatively high rate of oxygen flow. Thus, this method is useful only in facilities with sufficient oxygen supply, or in controlled home environments where a large oxygen tank is permissible. A disposable hyperbaric treatment bag with improved closure is disclosed in U.S. Pat. No. 5,029,579.

In U.S. Pat. No. 4,875,483, a combination layered dressing having an external low oxygen-permeability layer and an abutting internal oxygen permeable layer has been proposed. The relatively low permeability exterior layer is left attached for 3 to 72 hours creating hypoxia, and hopefully stimulating angiogenesis, following which this layer is removed. However, although the remaining, and now exterior layer is oxygen permeable, the layer nevertheless decreases oxygen transport, and thus hyperbaric treatment, by one of the methods previously described, may be necessary to elevate oxygen levels sufficiently to provide optimal healing.

It would be desirable to provide a dressing which is occlusive and which does not have to be periodically removed, but which promotes increased oxygen supply to the wound surface. It would be further desirable to provide a wound dressing which provides oxygen levels similar to those produced by moderate hyperbaric oxygen treatment without the necessity of maintaining a supply of pressurized oxygen. It would further be desirable to provide a wound dressing which can provide both the benefits of hypoxia and hyperoxia under these conditions by intermittently raising and lowering the oxygen level within the dressing.

SUMMARY OF THE INVENTION

The subject invention pertains to a multilayer dressing capable of supplying renewable chemically generated oxygen. The dressing may be applied over a hydrophilic colloid occlusive covering such as an alginate layer, and generates oxygen in situ for brief periods which can be repeated periodically without dressing removal.

BRIEF DESCRIPTION OF THE DRAWINGS

FIG. 7a illustrates a further experimental protocol for measuring oxygen transport into a hydrogel from the oxygen generating reservoir;

FIG. 7b is a plot of oxygen partial pressure for the protocol of FIG. 7a;

FIG. 8a is an experimental protocol for measuring oxygen concentration in the oxygen generating reservoir;

FIG. 8b is a plot of oxygen partial pressure measured for the protocol of FIG. 8a;

DESCRIPTION OF THE PREFERRED EMBODIMENTS

The subject wound dressing is designed to be able to produce a useful level of oxygen, for example sufficient oxygen to produce a hyperoxic condition, on an intermittent basis, followed by periods where little or no oxygen is supplied. The wound itself is normally covered by an occlusive, moist dressing, for example an alginate layer. This layer serves to isolate the wound from infection and in addition maintains the wound in a moist condition, generally recognized as encouraging the healing process, but allows permeation of oxygen, and optionally other healing aids such as growth factors, nutrients, enzymes, etc., which may be contained in the dressing. Although this layer may be periodically replaced, it is contemplated that it will remain undisturbed for appreciable periods of time.

The occlusive covering, in one embodiment of the subject invention, may be manufactured as an integral component of the subject wound dressing, optionally with a surrounding medical adhesive periphery to secure the dressing to the skin surface surrounding the wound. Hydrocolloids or gels other than alginates may be used for the occlusive dressing. Examples are, in particular, hydrogels formed using the following water soluble or water insoluble gums or resins, with or without known crosslinking agents: agarose, alkyl and hydroxyalkylcellulose, amylopectin, arabinoglactin, carboxymethylcellulose, carrageenan, eucheuma, fucoidan, furcellaran, gelatin, guar gum, gum agar, gum arabic, gum ghatti, gum karaya, gum tragacanth, hydroxethylcellulose, hydroxypropylcellulose, hypnea, keratin, laminaran, locust bean gum, pectin, polyacrylamide, poly(acrylic) acid and homologs, polyethylene glycol, poly(hydroxyalkyl methacrylate), polyvinyl alcohol, polyvinylpyrrolidone, propylene glycol alginate, starch and modified analogs, tamarind gum, N-vinyl lactam polysaccharides, and xantham gum. In addition, such hydrogels can also be formed by the copolymerization and crosslinking of both hydrophilic and hydrophobic monomers, such as hydroxyalkyl esters of acrylic and methacrylic acids, derivatives of acrylamide and methacrylamide, and N-vinyl-2-pyrrolidone, alkyl acrylates and methacrylates, vinyl acetate, acrylonitrile and styrene. A preferred hydrogel is INTRA SITE® gel, available from Smith and Nephew, Inc.

The wound dressing of the subject invention preferably contains an oxygen permeable membrane between the occlusive wound covering and the source of chemically-derived oxygen. The oxygen permeable membrane may be a durable, particularly more highly cross-linked hydrogel, or may be manufactured of the same material as the oxygen source reservoir, for example an alginate or other hydrogel, thus performing the duties of both reservoir and oxygen permeable membrane concurrently. However, the oxygen permeable membrane is preferably a microporous membrane or polymer film capable of transmitting oxygen but preferably incapable or inefficient in transmitting ionic substances in solution such as peroxide ion, hydroxide ion, and heavy metal ions. The oxygen permeable membrane may also be abutted, preferably on the side located furthest from the wound, with a layer of ion exchange resin particles or powders, or other ion adsorbing media. Preferably used are hydrophobic microporous membranes such as microporous teflon membranes. Other suitable microporous hydrophobic membranes include the VERSAPOR® hydrophobic membranes available from Gelman Sciences, Ann Arbor, Mich., and those disclosed in U.S. Pat. Nos. 4,374,232 and 5,126,189. Also suitable are microporous membranes which bear anionic or cationic charged sites, or both. Such microporous membranes are disclosed, for example, in U.S. Pat. Nos. 5,021,160 (acidic, for cation exchange), 5,151,189 and 5,269,931 (cationic, for anionic exchange), and 5,277,812 (interpenetrating, suitable for ultrapure water).

Because the oxygen chemically produced by the subject invention may include both gaseous oxygen as well as dissolved oxygen, hydrophilic membranes may also be suitable, particularly those of large pore size. For complete removal of anionic and cationic species, two or more membranes having different adsorption and gas transmissive abilities may be used, either as physically separate membranes, or as a laminate. Hydrophobic membranes having nominal pore sizes of from 0.01 µm to 10 µm, preferably 0.1 µm to 1.0 µm are preferred. It is desired to isolate known pathogens, a maximum pore size of 0.45 µm is preferred. The thickness of the membranes is not critical provided suitable oxygen permeability results. Suitable thicknesses may range from 0.2 mils to 4 mils, for example.

Suitable polymer film membranes, which are also preferably microporous, are those having high permeability to gases, particularly oxygen, and a structure which includes numerous polar or ionic groups capable of attracting ionic species. Polymer films having high oxygen permeability include cellulose acetate butyrate, ethyl cellulose, fluorinated ethylene propylene copolymer (FEP), low density polyethylene, and the like. The suitability of a particular film may be readily ascertained by in vitro tests, as described herein. A suitable film with respect to oxygen permeability is one which produces greater than 1 atm of oxygen partial pressure after a relatively short time period, i.e., 10 minutes or thereabouts, when tested in accordance with the procedure set forth in Example 1 or similar procedure. In like manner, the suitability of a polymer film for adsorbing ionic species may be evaluated by measuring the ionic species transported to an occlusive dressing both with and without the oxygen permeable membrane. With some catalyst systems, ionic species are not of concern due to their low concentration, and thus polymer films may be selected on the basis of oxygen permeability alone.

Abutting the outer surface of the oxygen permeable membrane, that is, the surface which will be located exterior to the wound with respect to the oxygen permeable membrane, is a reservoir containing a renewable, non-sustaining chemical oxygen source. While the term "reservoir" is used to describe the locus of the chemical oxygen source, it is appreciated that the physical device may contain an empty volume adapted to receive an oxygen generating liquid composition; may be a sponge-like or open-celled foam of natural, synthetic, or mixed natural/synthetic origin; or may comprise a solid, preferably an insoluble decomposition catalyst which acts upon a supplied liquid in contact therewith to chemically generate oxygen. The "reservoir" may further be a hydrogel containing solid or solubilized catalyst. By the term "renewable and non-sustaining" is meant that the oxygen generated will increase, remain at an elevated level, and then decrease, requiring further addition (renewal) of chemical oxygen source to supply further significant levels of oxygen such as are necessary to simulate hyperbaric conditions. The period during which elevated oxygen levels are supplied will range from several minutes to several hours.

In a preferred embodiment, the oxygen reservoir contains a solid which reacts with a supplied liquid to chemically generate oxygen. The solid may, for example, be potassium permanganate, and the liquid dilute hydrogen peroxide. Preferably, however, the solid is either insoluble or substantially insoluble in water, or is soluble but generates soluble moieties which are adsorbed or not transmitted by the oxygen permeable membrane or other adsorbent contained in the dressing. The preferred solid is manganese dioxide, which is virtually insoluble, is available in numerous forms from micropowders to large porous or non-porous granules, and which is effective to decompose hydrogen peroxide to oxygen and water. Other insoluble solids which decompose hydrogen peroxide or other oxygen-containing substances so as to chemically generate oxygen are also suitable. Examples may be selected from numerous transition metal oxides as well as transition metal compounds such as metal higher carboxylates, organic substances which catalyze peroxide decomposition such as naturally occurring or synthetic enzymes are also suitable. When potassium permanganate, ferric chloride, and other water soluble catalysts are used, these may be advantageously supplied in solution. For example, potassium permanganate may be added to an alginate reservoir from solutions with concentrations in the range of 1 mg/ml.

The solid oxygen decomposing substance may be loosely contained between the oxygen permeable membrane and an exterior cover of the wound dressing, but is preferably fixed in position by virtue of being surrounded by a containing material. This containing material may be a woven or gauze-like textile material of natural or synthetic fiber, fiberglass, or the like; a porous paper, e.g., such as is used for tea bags perforated plastic, or the like. The containing material may also advantageously itself be a microporous membrane, preferably a hydrophilic membrane such as those available from Gelman Sciences as SUPOR® microporous membranes. If microporous membranes are utilized, the pore size should in general be large, for example from 1 to about 20 µm. The microporous membrane may contain anionic or cationic charged sites or polar groups to adsorb cations and/or anions which might otherwise exude from the catalyst containing material.

Particularly with microporous membranes or perforated plastics material, the solids-containing layer may advantageously be a waffle-like structure with pockets containing the solid surrounded by sealed interstices which may be cut through with a razor or scissors, to facilitate supplying the wound dressing as a bulk material and cutting to size to fit the wound. In supplying in bulk, the various layers of the composite may be supplied separately, as on rolls, for example, or as a partially or fully integrated dressing. By partially integrated is meant that two or more layers are supplied as an integral unit, for example a hydrocolloid layer and oxygen permeable membrane layer unit; an oxygen permeable membrane layer and solid catalyst layer unit; and other combinations.

The solid oxygen-decomposing substance may also advantageously be fixed in position by a water permeable hydrogel or colloid, such as those described previously. In this case, the gel or colloid must be permeable to the oxygen source, for example aqueous hydrogen peroxide.

In addition to aqueous hydrogen peroxide, other oxygen sources may be utilized, for example organic hydroperoxides and organic peroxides such as benzoyl peroxide. Aqueous hydrogen peroxide in concentrations of 0.1 to about 10 weight percent, preferably 1 to 3 weight percent, and most preferably about 3 weight percent are preferred. When hydrogen peroxide or other hydroperoxide or peroxide is utilized as the oxygen source with manganese dioxide or other solid catalyst as the decomposition catalyst, the amount of catalyst is selected so as to decompose the amount of oxygen source added over a time period ranging from a desirably short time, for example 10 minutes, to an extended time generally not to exceed three to four hours. Other inorganic peroxides such as sodium peroxide may also be used. However, in such cases, it may be necessary to keep the dressing dry prior to application over the wound. The oxygen source may further comprise a biochemical supply, i.e., one where a non-pathogenic bacterium, algae, or other microorganism is encapsulated in hydrogel and produces oxygen by photosynthesis or other biochemical oxygen generating process. The term "chemical" as used herein includes biochemical means of producing oxygen.

To counteract any tendency for the dressing, during oxygen generating quiescent periods, to create excessive hypoxia, a minor amount of a continuous, low level, oxygen generating source such as that disclosed in U.S. Pat. No. 4,507,285 may be included within the dressing.

The amount of solid catalyst utilized may be easily selected by routine experimentation, taking into account first, the oxygen source charge (amount and concentration) and the desired time of oxygenation; and second, the activity of the catalyst, its state of subdivision, and the diffusion rates of the containing material used. Solid catalysts have activities proportional to their surface area, for example, and thus finely divided manganese dioxide powder will decompose a fixed amount of hydrogen peroxide at a much greater rate than coarse manganese dioxide granules. Moreover, if the manganese dioxide is encompassed within a gel, the decomposition rate will be lowered, as the rate will be dependent upon the rate of diffusion of hydrogen peroxide into the gel. The containing gel may also perform the function of absorbing the oxygen source, thus being the chemical oxygen source "reservoir" as well. Amounts of manganese dioxide in powder form of about 20 µg/cm$^2$ of dressing area are suitable. Potassium permanganate applied in solution form to result in from 1–30 µg/cm$^2$ are also suitable. The amount of catalyst may be determined in any given case through routine experimentation.

The decomposition catalyst may be contained within a foam. For example, an open-celled polyurethane foam may be prepared by reacting an isocyanate component with a polyol component, one or both of the latter containing ground manganese dioxide. The oxygen source, i.e. hydrogen peroxide, may then be absorbed into the foam whereupon it will be decomposed to produce oxygen. Likewise, other foams, including those of biologically derived materials, such as collagen sponge prepared by the method of U.S. Pat. Nos. 4,193,813 or 4,703,108 may be used.

The oxygen source may be absorbed by the containing material, as described previously may be absorbed by a separate absorbing layer, or may be introduced into a chamber whose depth in a direction orthogonal to the wound surface dictates the volume of oxygen supplying solution to be administered.

For example, a separate hydrogel or open-celled foam layer may be used to absorb the oxygen supply solution. The thickness of this layer may be varied depending upon the time of treatment desired for a given catalyst amount and configuration. Alternatively, an initially empty space may be provided, with an opening closable by adhesive tape or screw-on lid; or double fittings may be provided for ingoing fresh oxygen source fluid and outgoing spent fluid. These fittings may be any kind of simple closure, or may be adapted to mate with standard IV fittings. Even though the subject wound dressings are generally not used in such a manner so as to continuously oxygenate a wound, the latter mentioned method may be suitable for bed-ridden patients or those who ambulate with the aid of a wheelchair, as the oxygen supply fluid may simply be disconnected or the supply valve turned off for the appropriate quiescent interval.

The invention may be further understood with reference to the drawings, which are by way of illustration only, and should not be construed as limiting the scope of the invention.

Figure 1:
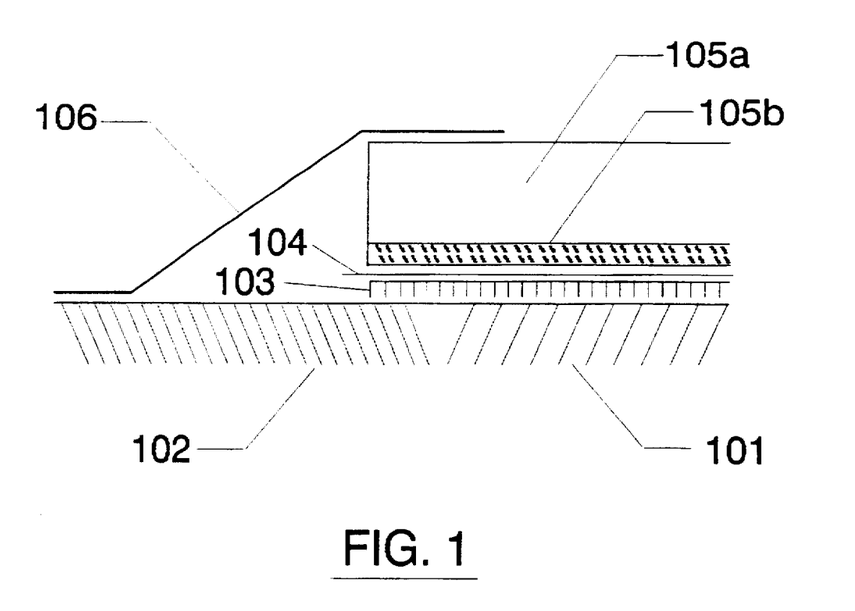
FIG. 1 illustrates a cross-section of one embodiment of the subject invention wound dressing showing the oxygen permeable membrane, oxygen reservoir, and occlusive wound covering.

FIG. 1 illustrates a patient's epidermal layer 102 with wound cavity 101. An occlusive covering, preferably a hydrocolloid or gel 103 is applied, and over this, an oxygen permeable membrane 104. Lying atop the oxygen permeable membrane is the oxygen supply reservoir 105, in this case a two layer hydrogel, the first layer 105b containing particles of manganese dioxide decomposition catalyst, the second layer 105a providing additional absorbance for the oxgyen source. A single, thicker hydrogel layer may be used as well. The assembly is held to the body surf ace by adhesive tape 106. In use, to reservoir 105 will be added a dilute solution of hydrogen peroxide, c.a. 3% concentration, which may simply be poured onto the reservoir gel. The surrounding skin surface may then be dried, and the whole wrapped or covered with a relatively oxygen impermeable film, such as polyvinylchloride or polyvinylidene chloride. SARAN® plastic wrap is suitable, for example. The thickness of reservoir gel 105 is selected to provide a period of oxygenation of preferably from 20 minutes to two hours at the given catalyst concentration. The oxygen generated passes through oxygen permeable membrane 104 and occlusive covering 103 to the wound 101, where the maximum oxygen tension generated will approach from 2 to about 5 atmospheres relative to air.

Figure 2A:
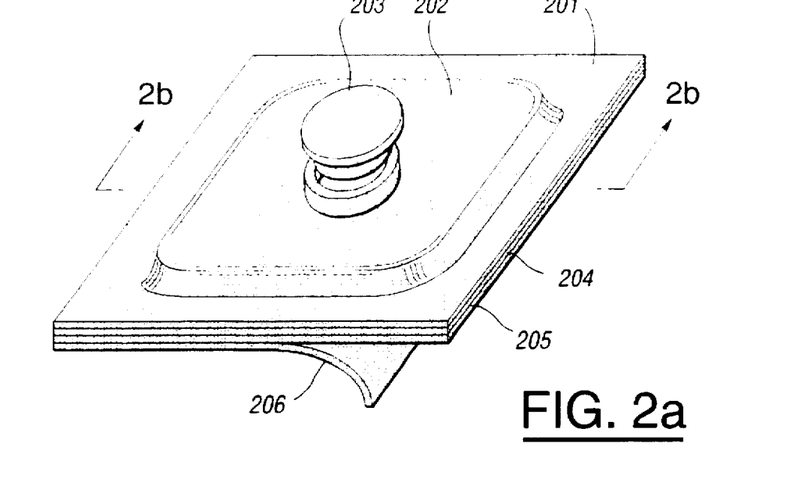
FIG. 2a illustrates a cross-section of a further embodiment of the subject invention suitable for manufacture in a variety of finite sizes.
Figure 2B:
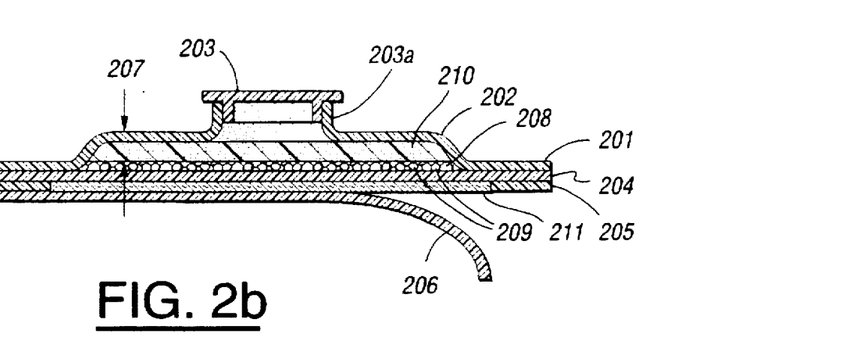
FIG. 2b is a cross-section of FIG. 2a across A—A.

With reference to FIGS. 2a and 2b, a wholly integrated wound dressing as might be supplied in a variety of finite sizes is illustrated, optionally also with an integral occlusive wound dressing and optional integral adhesive surround an d release layer. In FIG. 2a, the cover is shown at 201, preferably of low permeability material. The central portion of the cover contains a raised area 202 fitted with a closable cap 203 as might be provided on the exterior of an air mattress or inflatable toy, for example. Below the cover is oxygen permeable membrane 204, optional adhesive surround 205, and optional peelable release layer 206, shown partially peeled away.

Figure 2C:
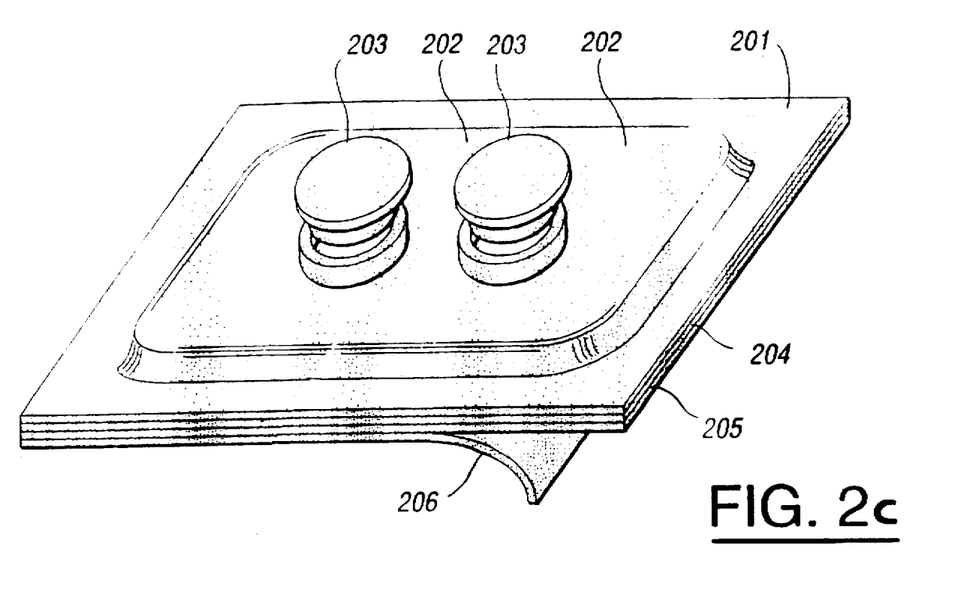
FIG. 2c illustrates a wound dressing corresponding to one embodiment of the subject invention, having an inlet for oxygen generating solution and an outlet for spent solution.

FIG. 2c represents a wound dressing having two closeable caps 203, one for inlet of oxygen generating solution, and one to remove spent oxygen generating solution. The remaining constituents of FIG. 2c are the same as FIGS. 2a and 2b whose description will not be repeated.

In FIG. 2b is a cross-section of the dressing of FIG. 2a across A—A. At 201 is the top cover with raised portion 202. Opening 203a is closed with press-on cap 203, while the oxygen permeable membrane and adhesive surround are shown at 204 and 205. At 206 is the release layer partially peeled away. In cavity 207, formed between top cover portion 202 and catalyst hydrogel layer 208 containing manganese dioxide granules 209 may be positioned an open-celled foam 210, as shown, a hydrogel, or the cavity may be left empty, in any case, to receive the oxygen supply solution. At 211 is shown the optional hydrogel occlusive wound covering layer.

Figure 3A:
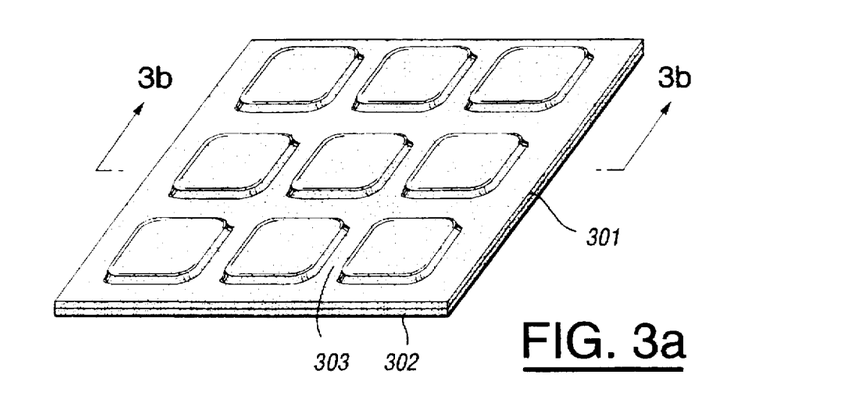
FIG. 3a illustrates one embodiment of a containing material for an oxygen supply solution decomposition catalyst.
Figure 3B:
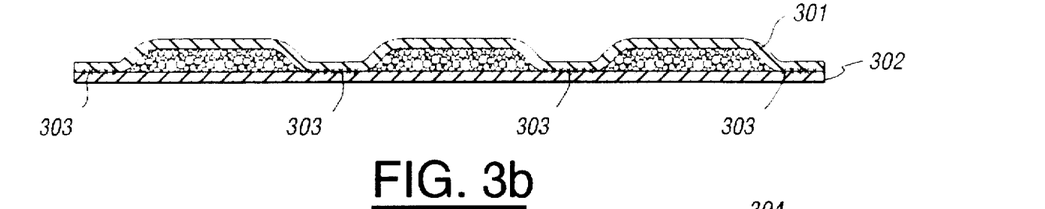
FIG. 3b is a cross-section of FIG. 3a across B—B.
Figure 3C:
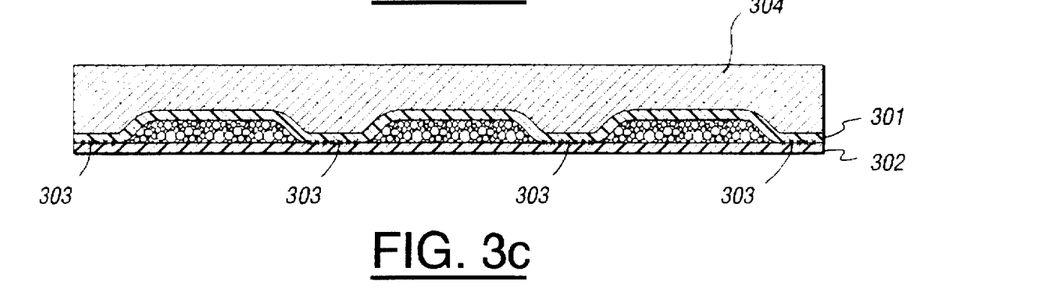
FIG. 3c is a further embodiment of a wound dressing of the subject invention.

In FIG. 3a is shown a further embodiment. In this case, a waffle-shaped containing material 301, which may be a hydrophilic microporous membrane or perforated plastic film, is bonded to oxygen permeable membrane 302 along areas 303, the raised projections containing manganese dioxide granules, shown in FIG. 3b, which is a cross-section of FIG. 3a along B—B. At FIG. 3c is a further embodiment showing the presence of cast-on hydrogel layer 304 adapted to receive the oxygen supply solution. The raised projections in FIGS. 3a, 3b, and 3c may be virtually unnoticeable, as the required amount of catalyst is very small.

Figure 4A:
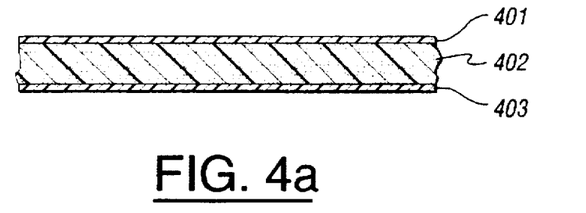
FIGS. 4a–4c illustrate yet further embodiments of various aspects of the subject dressings in cross-section.
Figure 4B:
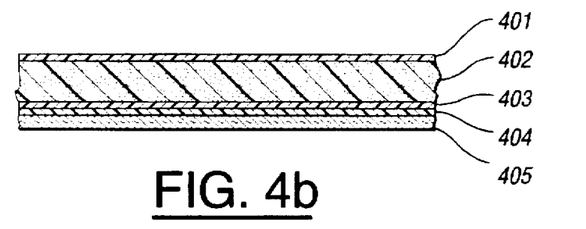
Figure 4C:
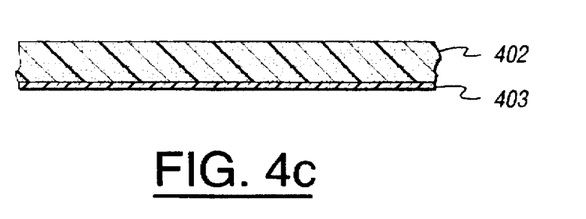

FIG. 4a illustrates an alternative embodiment where the oxygen supply solution requires no separate catalyst to generate oxygen. At 401 is a low oxygen permeable cover, at 402 an open-celled foam reservoir to receive the renewable oxygen supply solution, and at 403, an oxygen permeable membrane. At FIG. 4b is an alternative embodiment containing the same features, similarly numbered, as FIG. 4a, except in this case, two oxygen permeable membranes 403 and 404 are used, with the optional occlusive wound covering layer at 405. A further embodiment shown in FIG. 4c includes only the foam oxygen supply reservoir 402 and oxygen permeable membrane 403, and is designed to be applied, saturated with oxygen supply solution, and wrapped with low permeability plastic wrap.

EXAMPLE 1

Figure 5:
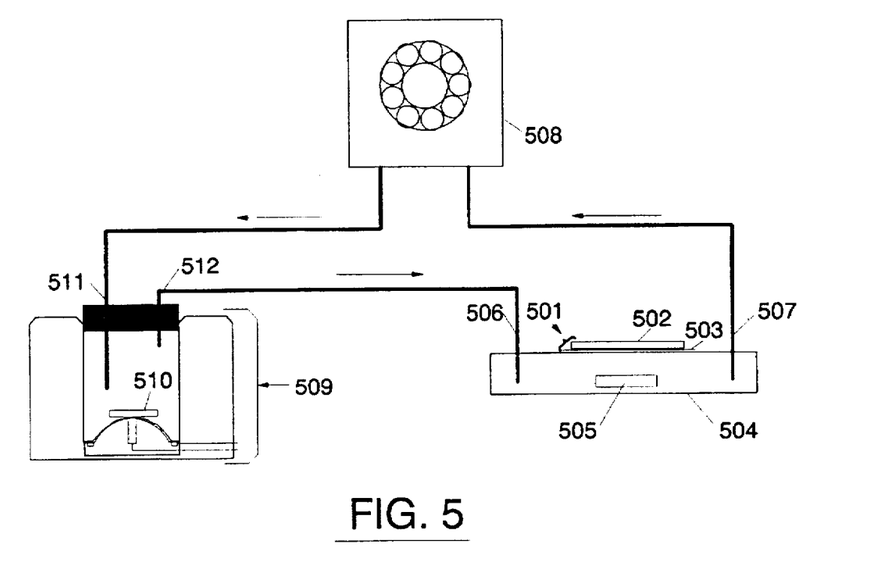
FIG. 5 illustrates an experimental apparatus to measure oxygen concentration generated by a wound dressing in accordance with the subject invention.
Figure 6:
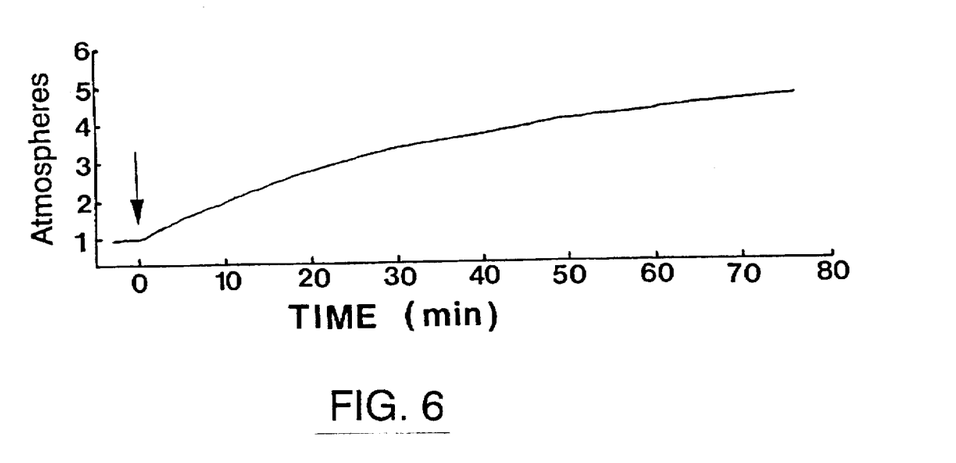
FIG. 6 is a plot of oxygen concentration v. time for a wound dressing tested as disclosed in FIG. 5.

With reference to FIG. 5, a test apparatus was assembled to demonstrate the effectiveness of the subject invention in elevating oxygen concentration. The test apparatus consisted of a 10 cm$^2$ test area wound dressing 501 consisting of a 10 cm$^2$ alginate gel 502 containing 0.5 mg of potassium permanganate over a teflon microporous membrane 503 mounted in a test chamber consisting of a standard petri dish 504 containing magnetic stirring bar 505, into which water inlet 506 and outlet 507 enter, and which are connected on the outlet side to peristaltic pump 508 pumping at the rate of 10 ml/min to a measuring chamber 509 containing a Clark polarographic oxygen electrode 510 (available from Rank Bros., Cambridge, U.K.) water inlet 511 and outlet 512. The oxygen permeable membrane is in contact with the water in the test chamber. Total volume of circulating water is 90 ml. The electrode is allowed to equilibrate to ambient conditions (c.a. 22° C., 1 bar air), following which to the hydrogel layer is added 1 ml 3% aqueous hydrogen peroxide. FIG. 6 shows a plot of oxygen in partial pressure atmospheres (1 atmosphere equals the oxygen concentration supplied by air at one atmosphere) with respect to time. The arrow indicates the point of hydrogen peroxide addition. As can be seen, the oxygen concentration rapidly increases, with a two-fold increase in oxygen concentration occurring after only about ten minutes, the concentration rising to c.a. 5 atm after 70 minutes. This concentration is substantially the same as that of a topical hyperbaric chamber employing pure oxygen at c.a. 1 atm or slightly above. Experiments employing manganese dioxide in place of potassium permanganate yield virtually identical results.

EXAMPLES 2-3

Figure 7:
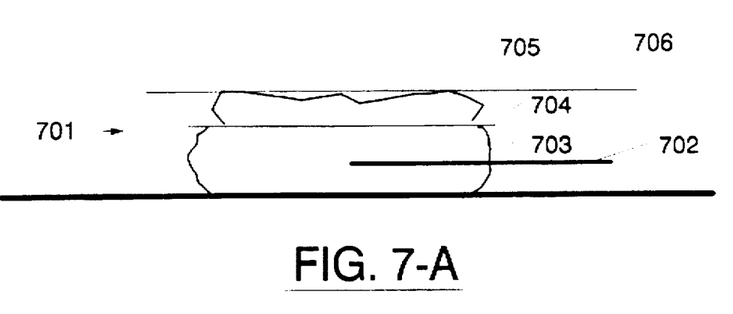

A further test was made in accordance with FIGS. 7 and 8a, with the results displayed in FIGS. 7b and 8b. In FIG. 7a, a hydrogel layer 703 simulates an occlusive wound dressing into which a TOPS (Tissue Oxygen Probe System, manufactured by Innerspace Inc., Irvin, Calif.) oxygen sensing probe 702 is inserted. Located superficial to the hydrogel 703 is teflon gas-permeable membrane 704, a hydrogel reservoir 705 containing 0.5 mg potassium permanganate per gram of hydrogel, and superficial to the reservoir, a wrap 706 of relatively impermeable SARAN® wrap film. Oxygen generation was initiated by addition of 0.2 ml 3% hydrogen peroxide to hydrogel reservoir 705. FIG. 7b indicates an approximately 50% increase in oxygen partial pressure after a period of 34 minutes.

Figure 8:
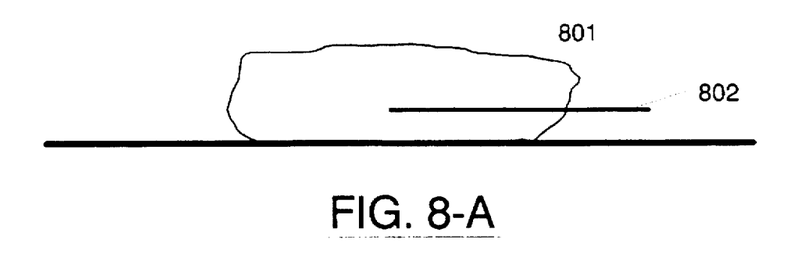

In FIG. 8, the measuring oxygen probe 802 was inserted directly into the hydrogel reservoir 801 for measurement of oxygen generated in the reservoir itself. Hydrogen peroxide (0.1 ml) of only 0.3% concentration was used. The available oxygen for transport more than doubled over a period of 24 minutes, as shown by FIG. 8b.

EXAMPLE 4

Testing for the oxygen-producing dressing utilized a rabbit ear ischemic ulcer model where a full thickness wound was created on the inner surface of the rabbit's ear. Skin and subcutaneous tissue were removed down to the perichondrium. The oxygen measuring probe was inserted into the perichondrium and over that was placed a hydrogel (INTRA SITE® gel, Smith & Nephew, Inc.). Superficial to the hydrogel was a Teflon oxygen permeable membrane, while superficial to the membrane was alginate impregnated with potassium permanganate solution which acted as the catalytic portion of the dressing. The hydrogen peroxide oxygen source was then applied to the alginate portion of the dressing, whereafter a SARAN® wrap was placed on top of the entire construct to help seal in the oxygen so that it would encourage diffusion directionally into the wound rather than out through the SARAN® wrap which is, of course, relatively impermeable.

Figure 9A:
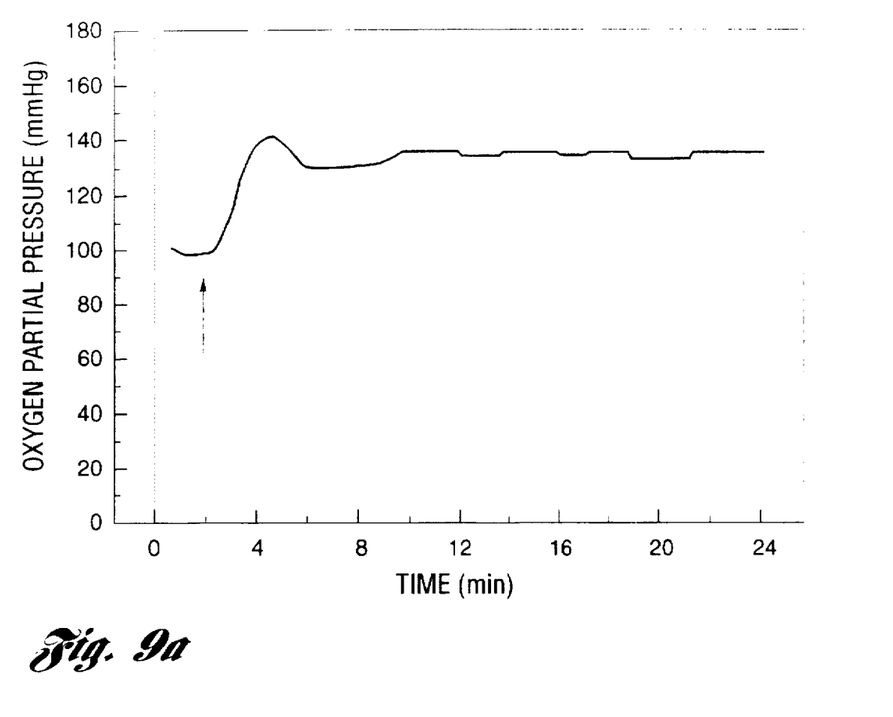
FIG. 9a is a plot of oxygen partial pressure versus time resulting from the in vivo protocol of Example 4 illustrating increase in oxygen concentration in the perichondrium following hydrogen peroxide addition.
Figure 9B:
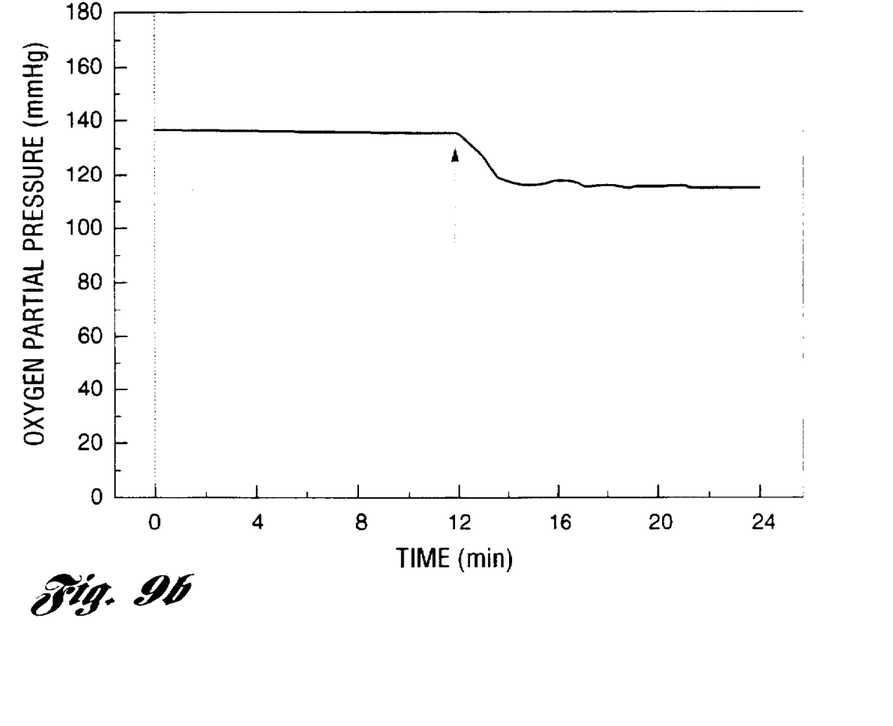
FIG. 9b is a plot of oxygen partial pressure versus time showing decrease in perichondrium oxygen level following dressing removal.

The measured oxygen concentration in the perichondrium is shown in FIG. 9a, where oxygen partial pressure increases from about 100 mm Hg to a relatively constant elevated level of c.a. 138 mm Hg after only 8 minutes. FIG. 9b shows that the oxygen level rapidly decreases after dressing removal. The duration of increased oxygen concentration may be adjusted by manipulating catalyst concentration and amount of hydrogen peroxide added. The arrows in FIGS. 9a and 9b indicate the points at which hydrogen peroxide addition and dressing removal, respectively, occur.

All manner of surface wounds may be treated by the method of the subject invention, including burns and scalds, venous and stasis ulcers, diabetic foot ulcers, refractory osteomyelitis, pyoderma gangrenosum, and necrotizing fascitis. Duration and repetition of treatment may be decided on a case by case basis, but generally at least two to four treatments of from 20 minutes to 2 hours, preferably 90 minute duration, are performed weekly until healing is progressed to the point where hypoxia is no longer of concern and healing may occur without increased oxygen tension.

As the danger of systemic oxygen toxicity as well as the danger of severe vasoconstriction common with systemic hyperbaric oxygen are of severely lessened concern, multiple daily treatment regimens may be implemented. These treatment periods are interspersed with "oxygen quiescent" periods where the oxygen tension of the wound approaches normal or even hypoxic levels, to stimulate angiogenesis.

The oxygen generating wound dressing, if not supplied with an integral cover, is wrapped with a low oxygen permeability outer wrap, preferably a non-porous polymeric film such as polyvinyl chloride or polyvinylidene chloride. SARAN® wrap is suitable, for example. Some additional suitable materials for this layer include, for example, polyethylene, polypropylene, polyvinylidene chloride, polyethylene terephthalate and other polyesters, and polyamides, as well as laminates of two or more of these layers with each other or with additional layers, such as foil, paper, various fabrics, etc. but in these cases preferably with the polymer layer on the inside. The outer wrap, or cover, may also be manufactured integral with all or a portion of the oxygen generating wound dressing, as previously discussed. It is preferred that the outer wrap have low oxygen permeability. However, even films with somewhat high oxygen permeability may be used, as under these conditions, sufficient oxygen is still presented to the wound surface.

Because of the lack of any need for pressurized oxygen or hyperbaric chamber, even those of the disposable polyethylene type, it is possible for the patient in many cases to be ambulatory and proceed with normal day-to-day activities The depth of the oxygen generating wound dressing is rather thin, and thus may often be worn unnoticed under shirts, blouses, pants, shirts, and other normal wearing apparel. Furthermore, as only an oxygen supply solution is required, optionally with a low oxygen permeability plastic film, travel is facilitated. The preferred treatment solution, 3% hydrogen peroxide, is readily available worldwide, as is also polymeric film such as SARAN® wrap.

Having now fully described the invention, it will be apparent to one of ordinary skill in the art that many changes and modifications can be made thereto without departing from the spirit or scope of the invention as set forth herein.

What is claimed is:

1. An oxygen-generating wound dressing suitable for periodically increasing the oxygen supply to a wound, comprising:
   a) an oxygen permeable membrane; and
   b) an oxygen supply reservoir proximate said oxygen permeable membrane and adapted to receive an aqueous solution containing a solute, said solute capable of renewably and non-sustainingly chemically generating oxygen, and
   c) a catalyst or enzyme contained within said wound dressing, said catalyst or enzyme capable of decomposing said solute to generate oxygen, said periodic increase in oxygen supply renewable indefinitely by addition of further aqueous solution.

2. The wound dressing of claim 1 wherein said oxygen supply reservoir contains a solid catalyst suitable for producing oxygen from said aqueous solution.

3. The wound dressing of claim 2 wherein said solid catalyst is substantially insoluble in water.

4. The wound dressing of claim 3 wherein said solid catalyst comprises manganese dioxide.

5. The wound dressing of claim 2 wherein said catalyst comprises an alkali or alkaline earth permanganate.

6. The wound dressing of claim 1 wherein said aqueous solution comprises hydrogen peroxide in a concentration of about 0.1 to about 10 weight percent based on the weight of the solution.

7. The wound dressing of claim 1 further comprising a low oxygen permeability cover located proximate to said oxygen supply reservoir on a side of said oxygen supply reservoir remote from said oxygen permeable membrane.

8. The wound dressing of claim 1 wherein said oxygen supply reservoir contains a catalyst effective to decompose hydrogen peroxide, said catalyst located within a containing material.

9. The wound dressing of claim 8 wherein said containing material is selected from the group consisting of hydrogels, open-celled foams, and collagen foams.

10. The wound dressing of claim 9 wherein said reservoir further contains a second hydrogel, open-celled foam, or collagen foam adapted to absorb a solution of hydrogen peroxide.

11. The wound dressing of claim 1, comprising:
   a) an oxygen permeable membrane having a first side adapted to be located proximate to a wound surface and a second side;
   b) a solid hydrogen peroxide decomposing catalyst contained within a containing material, the shape of said containing material adapted to be substantially contiguous with said second side of said oxygen permeable membrane; and
   c) a hydrogen peroxide solution-receiving reservoir.

12. The wound dressing of claim 11 wherein said hydrogen peroxide solution-receiving reservoir comprises said containing material.

13. The wound dressing of claim 1 wherein said oxygen permeable membrane comprises a microporous membrane.

14. The wound dressing of claim 1 wherein said oxygen permeable membrane and said oxygen supply reservoir comprise the same material of construction.

15. The oxygen-generating wound dressing of claim 1, further comprising a growth promoting amount of one or more human growth factors.

16. A method for renewably and non-sustainingly increasing the oxygen tension in surface wounds, comprising:
   a) applying over the surface of said wound an oxygen generating wound dressing comprising:
      i) an oxygen permeable membrane having a size adapted to substantially cover said wound;
      ii) a chemical oxygen supply reservoir abutting said oxygen permeable membrane on the side of said membrane most distant from said wound;
   b) supplying to said oxygen supply reservoir an oxygen supply solution containing a solute, said solute capable of chemically generating oxygen within said reservoir by catalytic decomposition, and
   c) a catalyst or enzyme contained within said wound dressing, said catalyst or enzyme capable of decomposing said solute to generate oxygen.

17. The method of claim 16 wherein said oxygen supply solution comprises aqueous hydrogen peroxide, and wherein said reservoir contains a solid catalyst capable of decomposing said aqueous solution of hydrogen peroxide.

18. The method of claim 17 wherein said solid catalyst is selected from the group consisting of an alkali or alkaline earth permanganate, manganese dioxide, and mixtures thereof.

19. The method of claim 17 wherein said solid catalyst is located within a containing material.

20. The method of claim 19 wherein said containing material is selected from the group consisting of hydrogels, open-celled polymeric foams, and collagen foams.

* * * * *